United States Patent [19]

Davis, Jr. et al.

[11] Patent Number: 5,036,193
[45] Date of Patent: Jul. 30, 1991

[54] EARTHEN CORE ANALYZING MEANS AND METHOD

[75] Inventors: Lorne A. Davis, Jr.; Timothy J. Hart; Robert M. Moss, all of Houston; Gregory P. Pepin, Sugarland, all of Tex.

[73] Assignee: Texaco Inc., White Plains, N.Y.

[21] Appl. No.: 457,213

[22] Filed: Dec. 26, 1989

[51] Int. Cl.$^5$ .......................................... G01N 23/06
[52] U.S. Cl. ....................................... 250/255; 378/4; 378/51; 73/38
[58] Field of Search ................ 250/255; 73/38; 378/4, 378/51, 52, 54, 56, 57, 53

[56] References Cited

U.S. PATENT DOCUMENTS 4,782,501 11/1988 Dixon, Jr. ............................ 250/255

Primary Examiner—Carolyn E. Fields
Assistant Examiner—Drew A. Dunn
Attorney, Agent, or Firm—Robert A. Kulason; James J. O'Loughlin; Ronald G. Gillespie

[57] ABSTRACT

An earthen core analyzer includes a test cell which contains an earthen core. A tomographic system is used for testing the earthen core and provides signals corresponding to the tests. While the earthen core is being tested, a fluid is provided to the earthen core as part of the testing. The signals from the tomographic system are used to determine a porosity of the earthen core.

6 Claims, 2 Drawing Sheets

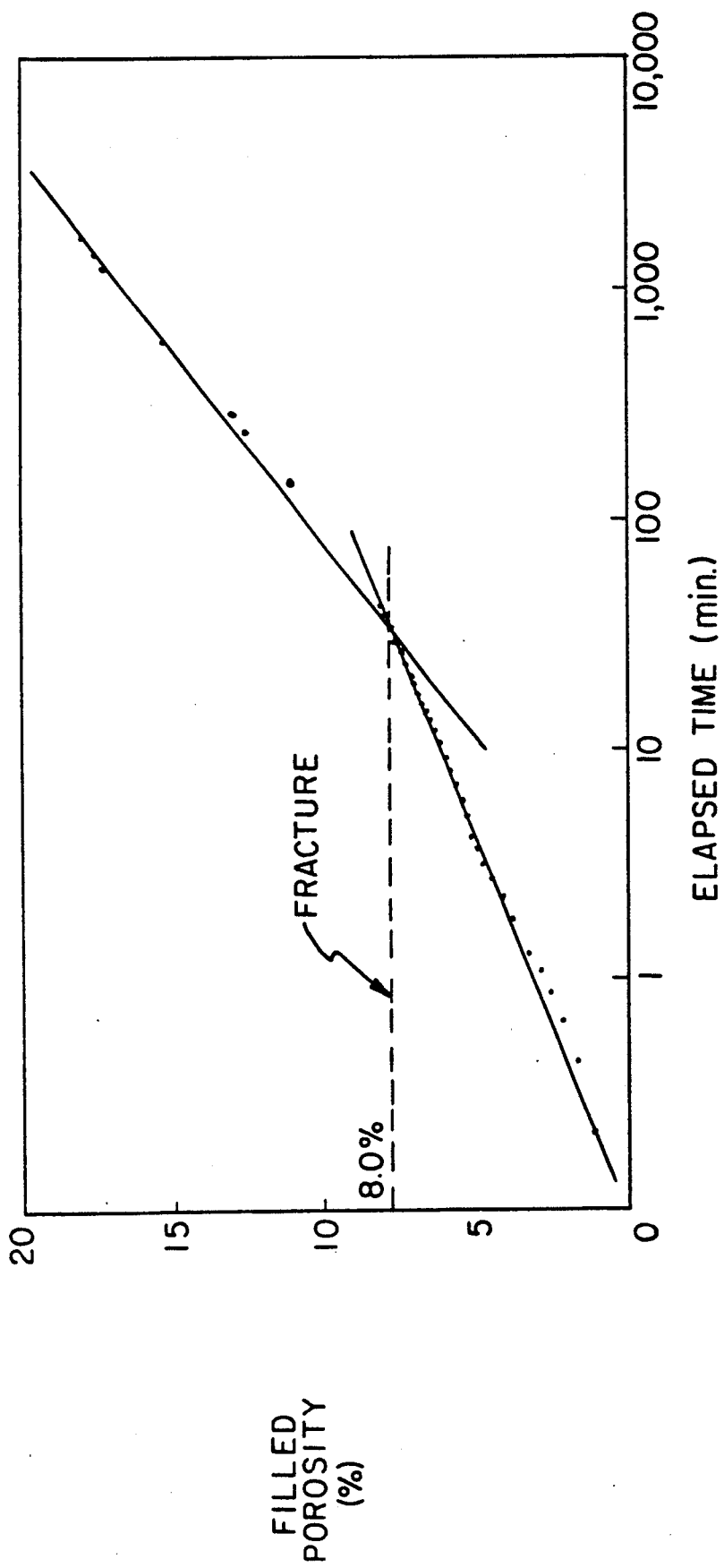

EARTHEN CORE ANALYZING MEANS AND METHOD

BACKGROUND OF THE INVENTION

1. Field of the Invention

The present invention relates to analyzing means and methods in general and, more particularly, analyzing means and methods for analyzing an earthen core.

2. SUMMARY OF THE INVENTION

An earthen core analyzer includes a test cell which contains an earthen core. A tomographic system is used for testing the earthen core and provides signals corresponding to the tests. While the earthen core is being tested, a fluid is provided to the earthen core as part of the testing. The signals from the tomographic system are used to determine the porosity of the earthen core.

The objects and advantages of the invention will appear more fully hereinafter from a consideration of the detailed description which follows, taken together with the accompanying drawings wherein one embodiment of the invention is illustrated by way of example. It is to be expressly understood, however, that the drawings are for illustration purposes only and are not to be construed as defining the limits of the invention.

DESCRIPTION OF THE DRAWINGS

FIG. 3 is a chart relating "FILLED POROSITY" to "ELAPSED TIME" from data accumulated in practicing the present invention.

DESCRIPTION OF THE INVENTION

The quantitative measurement and description of fracture porosity from cored reservoir samples can be critical to reserves estimation and production rate analysis. Conventional methods suffer from one or more of several drawbacks. Helium porosimetry and other displacement based techniques only measure overall porosity and fail to differentiate between normal porosity and fracture porosity. Thin section analysis is destructive to the core sample and can only reasonably examine a fraction of the core material. The method and apparatus of the present invention provides for the nondestructive analysis of fracture porosity. This method and apparatus provides both a quantitative measure of fracture porosity and also important qualitative information such as the interconnectedness and distribution of fracture porosity.

Figure 1:
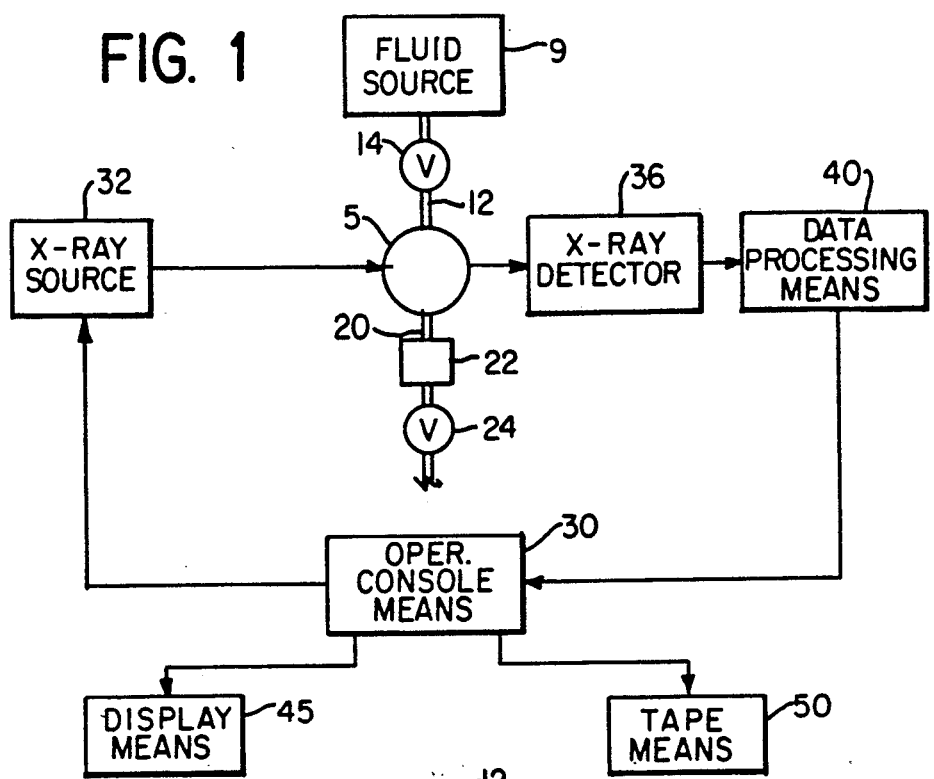
FIG. 1 is a simplified block diagram of an earthen core analyzing system as constructed in accordance with the present invention.

With reference to FIG. 1, a test cell 5 containing a core 7 of the earthen material to be analyzed, has connected to it a fluid source 9 by way of a line 12. The fluid over a finite period of time will fill test cell 5 and flow through test cell 5 and exit by way of a line 20. Test cell 5 is filled to a desired fluid pressure, with the measurements observed from a pressure transducer 22, due to a closed valve 24 stopping the fluid from exiting. To drain the fluid from test cell 5, valve 24 is opened.

While the front of the fluid is passing through test cell 5 an operator's console means 30 is used to control an X-ray source 32 to irradiate the core of earthen material in test cell 5 with X-rays. X-rays passing through the earthen core in test cell 5 are detected by an X-ray detector 36 which provides a signal corresponding to the detected X-rays. The signal corresponding to the detected X-rays provides a data processing means 40 which in turn provides data relating to the porosity of the earthen core to operator's console means 30. Operator's console means 30 provides output signals to display means 45 and to tape means 50.

Figure 2:
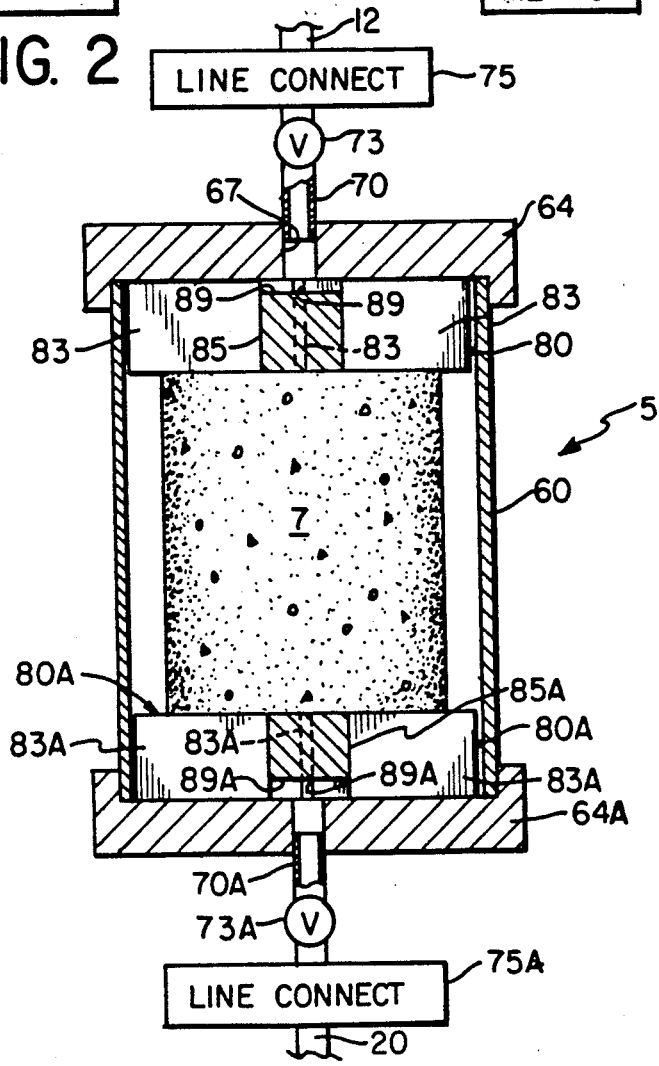
FIG. 2 is a detailed drawing of the test cell shown in FIG. 1.

With reference to FIG. 2 there is shown test cell 5 with the earthen core 7 within it. Test cell 5 is filled with a desired fluid pressure, with the measurements observed from pressure transducer 22. Test cell 5 includes an end cap 64. End cap 64 includes a passageway 67 having a line 70 attached thereto. This permits flow of fluid through line 70 through passageway 67 and hence through end cap 64. In line 70 is a valve 73 and line 70 also has a line connector 75 which permits connection of line 70 to line 12.

Test cell 5 also includes another end cap 64a, another line 70a with a valve 73a and a line connector 75a. All elements having the same numeric identification but with a letter suffix operate in the same manner as elements bearing the same numeric designation without a letter suffix.

Also shown in FIG. 2 are spacers 80 and 80a. In the embodiment as shown, spaces 80 and 80a have four wings each, 83 and 83a respectively, with the center elements 85 and 85a, respectively. Center elements 85 and 85a have slots 89 and 89a, respectively cut into them so that these slotted ends of spacers 80 and 80a may be placed against the passageways 67 and 67a, respectively. This allows fluid to flow from passageways 67 and 67a into the chamber formed by housing 60 and end caps 64, 64a. Thus, fluids flowing through test cell 5 will not only flow against the end of core 7 but will also pass around it so that it may also enter core 7 from either the end of core 7 or from the sides of core 7, depending on the permeability characteristic of core 7.

Let H correspond to the signal from X-ray detector. Usually H is defined by $$H = [(\mu - \mu_w)/\eta_w](1000) \tag{1}$$

in Hounsfield units, where $\mu$ is a linear attenuation coefficient for the specimen earth formation, and $\mu_w$ is the linear attenuation coefficient for water. Further $\phi$ is porosity, $\phi_f$ is fracture porosity, and $\phi$ is mass density.

The subscripts are as follows: r refers to rock material (with $\phi = 0$); f refers to invading fluid; c, o refers to an evacuated core (or air at one atmosphere), and c, f refers to a core filled with fluid.

From the general mixture rule for calculating $\mu$ for a mixture or compound $$\mu_{c,f} = \mu_r \phi_r (1-\phi) = \mu_f \phi_f \phi \tag{2}$$

$$\mu_{c,o} = \mu_r \phi_r (1-\phi) \tag{3}$$

These can be manipulated using the definition of response, H, where $$H_{c,f} = [(\mu_{c,f} - \mu_w)/\mu_w](1000)$$

$$H_{c,o} = [(\mu_{c,o} - \mu_w)/\mu_w](1000)$$

$$\phi = (H_{c,f} - H_{c,o})/(1000 + H_f) \tag{4}$$

More generally $$\phi = (H_{c,f} - H_{c,o})/(H_f - H_o) \tag{5}$$

where $H_o$ = the measured CT response to vacuum (or air).

where $H_{c,f}$ is measured with fluid in core, $H_{c,o}$ is measured with core filled with one atmosphere of air or evacuated, and $H_f$ is the response measured on a sample of the filling fluid at the filling conditions. $H_f$ and $H_o$ can be measured each time, or measured once and periodically checked. It is preferred that $H_f$ and $H_o$ be measured each time in the same chamber which holds the specimen core. Typically, $$1500 < H_c < 2500,$$

$$-500 < H_f < 1500,$$

$H_f$ for water = 0, and
$H_o$ for air is $\approx -1000$
$H_f$ is approximately 1100 for Xenon gas at 200 psig and room temperature.

The desired invading fluid is chosen depending on the core porosity, permeability, and radius. A high electron density gas is used for a low permeability core. For a core with high porosity, a non-radiopaque fluid, such as brine or hydrocarbon can be used. For a core with high permeability, a viscous invading fluid, such as iododecane-doped (low porosity) or a non-doped (high porosity) mineral oil, such as Regal oil 460.

For a 20% $\phi$ and a typical response with a standard deviation of $\pm 2$, $\phi$ can be measured to 0.002 with an accuracy of 0.01.

I. MEASUREMENT OF WHOLE CORE

This method does not require a physical measurement of the sample rock volume, thus eliminating this as a source of error. For uniform whole cores, sometimes the dimensions may be measured. However, the core is invariably non-cylindrical to some extent and has imperfections on the surface that limit the accuracy of the computed core volume. Irregularly shaped pieces must have their volume measured by immersion in mercury with the mercury displacement measured as the core bulk volume. The industry is working at eliminating the handling of mercury and its general use in the lab due to its high toxicity.

II. MEASUREMENT OF FRACTURE POROSITY

Reservoir engineering calculations want a value of the connected fracture porosity. Typically this is important when the fracture permeability is several orders of magnitude greater than the matrix permeability.

The method of the present invention measures exactly this parameter and measures it directly. Equation (4) is used with $H_{c,f}$ measured at a time immediately after introduction of the fluid but before the matrix can be invaded. The fluid is chosen to give a reasonable H in the ($H_{f,c}$-$H_{o,c}$) and with a viscosity appropriate for the time scale set by the permeability. One skilled in the art may want to use Xe or a freon gas for very tight cores. With higher permeability cores, water or viscous hydrocarbon liquids can be used.

One can see in FIG. 2, that the rate of filling the pores of a core of Monterey shale changes over a period of time and actually exhibits two rates of filling. Thus straight lines plotted from the data intersect at approximately 8% filled porosity and corresponds to the fractured porosity.

The method of the present invention is independent of any assumptions of the fracture width or degree of filling of the fracture by geologic deposition.

Also important is the fact that the method of the present invention can be conducted on a core on which pressure is applied to simulate the true down-hole stress conditions. Thus $\phi_f$ can be measured with the core in a reservoir-stress condition. This may affect the $\phi_f$.

We claim:

1. An earthen core analyzing system comprising:
   test cell means for containing an earthen core, an earthen core located in the test cell means,
   tomographic means for testing the earthen core and providing signals corresponding thereto,
   means for providing a fluid to the earthen core as part of the testing of the earthen core, and
   porosity means for utilizing the signals from the tomographic means to determine a porosity of the earthen core; and
   in which the porosity means provides an output corresponding to the fracture porosity of the earthen core in accordance with a change in the rate of change of the signals from the tomographic means as the earthen core is filling with the fluid.

2. A system as describes in claim 1 in which the determining means determines the fracture porosity of the earthen core in accordance with the signal from the tomographic means and the following equation:

$$\phi = (H_{c,f} - H_{c,o})(100 = H_f),$$

where $\phi$ is the fracture porosity, $H_{c,f}$ is the signal H at the time when the fluid has reached the predetermined pressure level, $H_{c,o}$ is the signal H when there is no fluid in the earthen core, and $H_f$ is the signal when the tomographic means tests only the fluid.

3. A system as described in claim 1 in which the determining means determines the fracture porosity of the earth core in accordance with the signal from the tomographic means and the following equation:

$$\phi \times (H_{c,f} - H_{c,o})(H_f H_o)$$

where $\phi$ is the fracture porosity, $H_{c,f}$ the signal H at the times when the fluid as reached the predetermined pressure, $H_{c,o}$ is the signal H when there is no fluid in the core, $H_f$ is the signal when the tomographic means tests only the fluid, and $H_o$ is the measured response by the tomographic means of air.

4. An earthen core analyzing method comprising the steps:
   containing an earthen core in a test cell,
   testing the earthen core with tomographic means,
   providing signals from the tomographic means corresponding to the testing,
   providing a fluid to the earthen core as part of the testing of the earthen core, and
   utilizing the signal from the tomographic means to determine a porosity of the earthen core; and
   in which the utilizing step includes:
   providing an output corresponding to the fracture porosity of the earthen core in accordance with a change in the rate of change of the signals from the tomographic means as the earthen core is filling with fluid.

5. A method as described in claim 4 in which the output step includes:

determining the fracture porosity of the earthen core in accordance with the signal from the tomographic means and the following equation:

$$\phi = (H_{c,f} - H_{c,o})/(1000 + H_f),$$

where $\phi$ is the fracture porosity, $H_{c,f}$ is the signal H at the time when the fluid has reached the predetermine pressure level, $H_{c,o}$ is the signal H when there is no fluid in the earthen core, and $H_f$ is the signal when the tomographic means tests only the fluid.

6. A method as described in claim 4 in which the output step includes:

determining the fracture porosity of the earth core in accordance with the signal from the tomographic means and the following equation:

$$\phi = (H_{c,f} - H_{c,o})/(H_f - H_o),$$

where $\phi$ is the fracture porosity, $H_{c,f}$ the signal H at the time when the fluid as reached the predetermined pressure, $H_{c,o}$ is the signal H when there is no fluid in the core, $H_f$ is the signal when the tomographic means tests only the fluid, and $H_o$ is the measure response by the tomographic means of air.

* * * * *